United States Patent [19]

Hitzel et al.

[11] 4,157,395
[45] Jun. 5, 1979

[54] BENZENESULFONYL UREAS

[75] Inventors: Volker Hitzel, Hofheim am Taunus; Rudi Weyer, Kelkheim; Werner Pfaff, Hofheim am Taunus; Karl Geisen, Frankfurt am Main, all of Fed. Rep. of Germany

[73] Assignee: Hoechst Aktiengesellschaft, Frankfurt am Main, Fed. Rep. of Germany

[21] Appl. No.: 903,548

[22] Filed: May 8, 1978

[30] Foreign Application Priority Data

May 10, 1977 [DE] Fed. Rep. of Germany ....... 2720926

[51] Int. Cl.² .................. C07D 213/56; A61K 31/44
[52] U.S. Cl. ................................. 424/266; 546/285; 546/298; 546/316
[58] Field of Search .............. 260/294.8 F, 294.8 B, 260/294.8 C; 424/266

[56] References Cited

U.S. PATENT DOCUMENTS 4,066,639  1/1978  Weber et al. .................. 260/294.8 F Primary Examiner—Alan L. Rotman
Attorney, Agent, or Firm—Curtis, Morris & Safford

[57] ABSTRACT

Benzenesulfonyl ureas of the formula

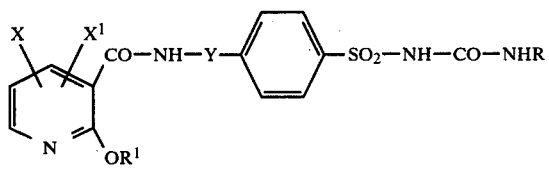

in which R, $R^1$, X, $X^1$ and Y have the defined meanings, and the salts thereof, process for preparing these compounds, pharmaceutical preparations containing them and their use for lowering the blood sugar level.

9 Claims, No Drawings

BENZENESULFONYL UREAS

The present invention relates to sulfonylureas of the formula

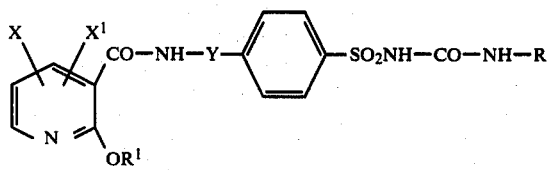

which, in substance or in the form of their salts, have hypoglycemic properties and which are distinguished by a strong and long lasting reduction of the blood-sugar level.

In the formula $R^1$ is alkyl with 3 to 8 carbon atoms, cycloalkyl, cycloalkylalkyl, alkylcycloalkyl, each of which having of from 5 to 9 carbon atoms, phenyl, which may be mono- or di-substituted by alkyl or alkoxy each of which having up to 4 carbon atoms, or by halogen, phenylalkyl with up to 3 carbon atoms in the alkyl moiety, which may be mono- or di-substituted in the phenyl nucleus by alkyl or alkoxy each having up to 4 carbon atoms, or by halogen, X and $X^1$ each is hydrogen, alkyl with up to 4 carbon atoms, alkoxy with up to 2 carbon atoms, halogen, Y is alkylene with 2 to 3 carbon atoms, R is alkyl with 1 to 6 carbon atoms, cycloalkyl, alkylcycloalkyl, cycloalkylalkyl, cycloalkenyl, alkylcycloalkenyl each having of from 5 to 9 carbon atoms, alkylcyclopentylmethyl, cyclohexenylmethyl, chlorocyclohexyl, bicycloheptenylmethyl, bicycloheptylmethyl, bicycloheptenyl, bicycloheptyl, nortricyclyl, adamantyl, benzyl.

The bridging member Y preferably is the group —CH$_2$—CH$_2$—.

X and $X^1$ may be identical or different. Compounds in which X and $X^1$ each is hydrogen or one of the substituents is hydrogen and the other halogen, preferably chlorine, or methyl, and those in which one of the substituents is chlorine and the other methyl, are particularly preferred. If $R^1$ is alkyl, it preferably has of from 4 to 8 carbon atoms.

The present invention furthermore relates to a proces for the manufacture of these sulfonyl ureas, to pharmaceutical preparations containing them or consisting of them and to the use of the sulfonyl ureas for the treatment of diabetes.

The process for the manufacture of the sulfonyl ureas comprises (a) reacting benzenesulfonyl-isocyanates, -carbamic acid esters, -thiolcarbamic acid esters, -ureas, -semicarbazides or -semi-carbazones, substituted in 4-position by the group

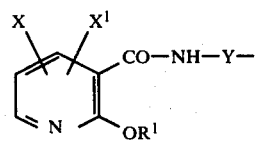

with an amine R-NH$_2$ or with its salts or reacting sulfonamides of the formula

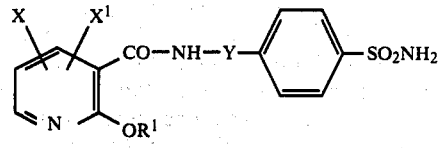

or their salts with R-substituted isocyanates, carbamic acid esters, thiocarbamic acid esters, carbamic acid halides or ureas, (b) splitting correspondingly substituted benzenesulfonyl-isourea ether, -isothiourea ethers, -parabanic acids or -halo-genformic acid amidines, (c) replacing the sulfur atom in benzenesulfonylthio ureas substituted by

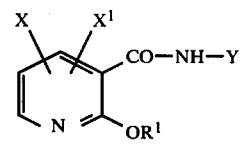

by oxygen, (d) oxidizing corresponding benzenesulfinyl or -sulfenyl ureas, (e) introducing into benzenesulfonyl ureas of the formula

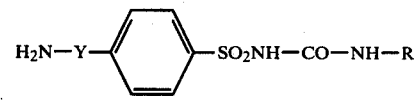

the radical

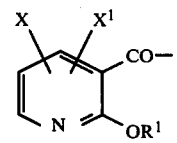

(f) reacting correspondingly substituted benzenesulfonyl halides with R-substituted ureas or with alkali metal salts thereof, or reacting correspondingly substituted benzenesulfinic acid halides or, in the presence of acid condensation agents, also correspondingly substituted sulfinic acids or alkali metal salts thereof, with N-R-N'-hydroxyurea and treating the reaction products with alkaline agents, if a salt formation is desired.

The abovementioned benzenesulfonyl-carbamic acid esters or -thiolcarbamic acid esters may possess an alkyl radical, an aryl radical or a heterocyclic radical in the alcohol moiety. Since this radical is split off during the reaction, its chemical constitution has no influence on the character of the final products and may thus vary within wide limits. The same applies to the N-R-substituted carbamic acid esters or the corresponding thiolcarbamic acid esters.

Suitable carbamic acid halides are in the first place the chlorides.

The benzenesulfonyl ureas to be used as the starting products of process (a) can be non-substituted or mono- or especially di-substituted at that side of the urea molecule which is opposite to the sulfonyl group. Since these substituents are detached during the reaction with amines, their character may vary within wide limits. In addition to alkyl-, aryl-, acyl- substituted benzenesulfonyl ureas or those substituted by heterocyclic compounds, benzenesulfonylcarbamoylimidazoles and similar compounds or bisbenzenesulfonyl ureas, which carry at one of the nitrogen atoms further substituents, for example methyl, may be used. Bis(benzenesulfonyl)ureas of this type or N-benzenesulfonyl-N'-acyl ureas may be treated with R-substituted amines and the salts formed may be heated to elevated temperature, especially of more than 100° C.

It is furthermore possible to start from R-substituted ureas or from those R-substituted ureas which carry one or especially two substituents at the free nitrogen atom and to react these ureas with benzenesulfonamides substituted in 4-position by

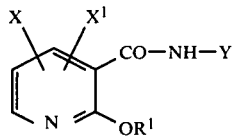

Suitable starting compounds of this kind are, for example, N-cyclohexylurea, the corresponding N'-acetyl, N'-nitro, N'-cyclohexyl, N,N'-diphenyl (in which case both phenyl radicals may also be substituted or be linked with one another directly or via a bridging unit, for example —$CH_2$—, —NH—, —O—, or —S—), N'-methyl-N'-phenyl, N',N'-dicyclohexyl ureas as well as cyclohexylcarbamoylimidazoles, -pyrazoles or -triazoles and furthermore those of said compounds which carry, instead of cyclohexyl, an other ubstituent covered by one of the definitions for R.

The benzenesulfonylparabanic acids, -isourea ethers, -isothiourea ethers or -halogenoformic acid amidines are advantageously split by alkaline hydrolysis. Isourea ethers may furthermore be split successfully in an acid medium.

The sulfur atom in the urea grouping of correspondingly substituted benzene sulfonylthioureas may be replaced by an oxygen atom in known manner, for example using oxides or salts of heavy metals or using oxidation agents, for example hydrogen peroxide, sodium peroxide, nitrous acid or permanganates.

The thioureas may alternatively be desulfurized by treating them with phosgen or phosphorus pentachloride. Chloroformic acid amidines or carbodiimides which are formed as an intermediary product in this process may be converted into the benzenesulfonylureas by suitable measures, for example by saponification or addition of water.

Benzenesulfinyl or benzenesulfenylureas are oxidized in known manner, for example using oxidation agents, such as, for example permanganate or hydrogen peroxide.

The acyl radical is introduced into the benzenesulfonyl ureas according to process (e) suitably by using a reactive derivative of an acid of the formula

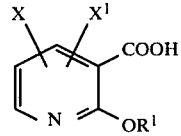

Suitable derivatives are, for example, halides or mixed anhydrides.

Examples of sulfonyl- or sulfinylhalides which may be employed according to the process (f) are especially the chlorides. A suitable acid condensation agent is, for example, thionylchloride or polyphosphoric acid.

The processes according to the invention may generally be carried out under considerably varying reaction conditions and be adapted to the circumstances in each case. For example, the reactions may be carried out in the absence or in the presence of solvents, at room temperature or at elevated temperature.

Depending on the character of the starting compounds employed, it may occur that the one or the other of the described processes in some cases gives the desired benzenesulfonyl urea only in low yields or even is not suitable for synthesizing this urea. In these relatively seldom observed cases, an expert may without difficulty synthesize the desired product by another of the described processes.

The compounds according to the invention may be converted into physiologically acceptable salts by known methods, for example by reacting them with bases, carbonates or amines. The compounds according to the invention have valuable pharmaceutical properties and are in particular distinguished by a hypoglycemic action. Thus, they are suitably used for the preparation of pharmaceuticals.

The hypoglycemic action of the benzenesulfonyl ureas of the invention may be tested in the following manner: The compounds are fed to normally nourished rabbits, as free compounds or in the form of their sodium salts, at doses of 10 mg/kg and the blood-sugar value is determined according to the known method of Hagedorn-Jensen, using an auto-analyzer or according to the hexokinase method over an extended period of time.

The decrease of the blood-sugar level in percent which has been determined upon oral administration of some of the compounds according to the invention, using the above test arrangement, is shown in the following table:

TABLE

| | Compound | Blood-sugar decrease in per cent after | | | | |
|---|---|---|---|---|---|---|
| | | 1 | 3 | 6 hours | 24 | 48/72 |
| 1. | N-[4-(2-<2-butoxy-5-chloro-nicotinamido>-ethyl))-benzenesulfonyl]-N'-cyclohexyl urea | 40 | 48 | 52 | 54 | 0 |
| 2. | N-[4-(2-<5-chloro-2-pentyl-oxynicotinamido>-ethyl)-benzenesulfonyl]-N'-methyl-urea | 44 | 55 | 45 | 0 | |
| 3. | N-[4-(2-<5-chloro-2-pentyl-oxynicotinamido>-ethyl)-benzenesulfonyl]-N'-propyl urea | 42 | 37 | 33 | 39 | 0 |
| 4. | N-[4-2-<-2-(4-methoxy-phenoxy)-nicotinamido>-ethyl)-benzenesulfonyl]-N'-(4-methyl-cyclohexyl) urea | 32 | 30 | 39 | 21 | 13/0 |
| 5. | N-[4-(2-<2-(4-methyl-phenoxy)-nicotinamido>-ethyl)-benzenesulfonyl]-N'-butyl urea | 17 | 24 | 36 | 8 | 0 |
| 6. | N-[4-2-<2-phenoxy-nicontinamido>-ethyl)-benzenesulfonyl]-N'-(3-methylcyclopentyl) urea | 19 | 14 | 26 | 40 | 0 |
| 7. | N-[4-(2-<2-phenoxy-nicotinamido>-ethyl)-benzenesulfonyl]-N'-cyclohexyl urea | 57 | 61 | 60 | 55 | 23/0 |
| 8. | N-[4-(2-<2-butoxy-5-chloro-nicotinamido>-ethyl)-benzenesulfonyl]-N'-(3-methyl-cyclopentyl) urea | 16 | 22 | 24 | 22 | 0 |

TABLE-continued

| Compound | Blood-sugar decrease in per cent after | | | | |
|---|---|---|---|---|---|
| | 1 | 3 | 6 | 24 | 48/72 |
| | | | hours | | |
| 9. N-[4-(2-<2-butoxy-5-chloro-nicotinamido>-ethyl)-benzenesulfonyl]-N'-(2,5-endo-methylencyclohexyl) urea | 19 | 19 | 24 | 12 | 0 |
| 10. N-[4-(2-<5-chloro-2-(4-methyl-cyclohexyloxy)-nicotinamido>-ethyl)-benzenesulfonyl]-N'-butyl urea | 5 | 10 | 22 | 21 | 10/0 |
| 11. N-[4-(2-<2-butoxy-5-chloro-6-methyl-nicotinamido>-ethyl)-benzenesulfonyl]-N'-butyl urea | 13 | 38 | 43 | 25 | 39/0 |

Acylaminoalkylbenzenesulfonyl ureas the acyl radical of which carries a 2-methoxy- or 2-ethoxynicotinic acid radical, certainly, have been described (cf. German Offenlegungsschrift No. 2,419,198), however, the hypoglycemic action of these compounds was not as strong and long lasting as that of the compounds according to the invention.

The benzenesulfonylureas of the present invention should be preferably employed for the manufacture of orally administrable preparations having a hypoglycemic action in the treatment of diabetes mellitus. They may be used as such or in the form of their salts or in the presence of compounds which lead to a salt formation. Suitable compounds for the latter purpose are, for example, alkaline agents, for example alkali metal or alkaline earth metal hydroxides, carbonates or bicarbonates.

As pharmaceutical preparations tablets are preferred which contain, in addition to the active ingredients, the usual carriers or auxiliaries, for example talc, starch, lactose, tragacanth, or magnesium stearate.

A preparation, which contains the above described benzenesulfonylureas as active ingredient, for example in the form of a tablet, a capsule or a powder with or without additives, is suitably brought into an appropriate dosage form. A suitable dose is that which is adapted to the efficiency of the benzenesulfonylureas employed and to the desired effet. The dosage per unit is suitably in the range of from about 1 to 100 mg, preferably of from 5 to 20 mg, however, higher or lower dosage units, which may be divided or multiplied prior to administration, may also be used.

The sulfonylureas according to the invention may be used for the treatment of diabetes mellitus both alone or in combination with other oral antidiabetics. Examples of the latter are not only hypoglycemic sulfonylureas, but also compounds of different chemical structure, such as, for example biguanides, especially the phenylethyl biguinide or dimethyl biguanide.

The following examples illustrate some of the possible variants which are suited for synthesizing the sulfonylureas according to the invention, without restricting the subject of the invention:

EXAMPLE 1

N-[4-(2-<2-butoxy-5-chloro-nicotinamido>-ethyl)-benzene-sulfonyl]-N'-cyclohexyl urea 6.1 g of 4-(2-<2-butoxy-5-chloro-nicotinamido>-ethyl)-benzenesulfonamide (m.p. 168°–169° C., prepared from 4-(2-aminoethyl)-benzenesulfonamide and 2-butoxy-5-chloro-nicotinic acid chloride) are dissolved in 70 ml of aceton and 7.5 ml of 2N sodium hydroxide solution. After cooling of the solution to 0° C., 1.9 g of cyclohexylisocyanate in 5 ml of aceton are added dropwise. The batch is stirred for 1 hour at 0° C. and for 4 hours at room temperature. Thereafter it is diluted with water until the double volume is reached, the solution is filtered and acidified with dilute acetic acid. The precipitate is reprecipitated from dilute ammonia solution with dilute acetic acid and recrystallized from methanol. The N-[4-(2-<2-butoxy-5-chloro-nicotinamido>-ethyl)-benzenesulfonyl]-N'-cyclohexyl urea thus obtained melts at a temperature of from 154° to 155° C.

In analogous manner there are obtained the following compounds:

N-[4-(2-<2-butoxy-5-chloro-nicotinamido>-ethyl)-benzenesulfonyl]-N'-methyl urea of m.p. 185°–186° C. (from methanol);

N-[4-(2-<2-butoxy-5-chloro-nicotinamido>-ethyl)-benzenesulfonyl]-N'-benzyl urea of m.p. 156°–159° C. (from methanol);

N-[4-(2-<2-butoxy-5-chloro-nicotinamido>-ethyl)-benzenesulfonyl]-N'-propyl urea of m.p. 126°–128° C. (from acetic acid ethyl ester);

N-[4-(2-<2-butoxy-5-chloro-nicotinamido>-ethyl)-benzenesulfonyl]-N'-butyl urea of m.p. 161°–163° C. (from acetic acid ethyl ester).

In analogous manner there are obtained from 4-(2-<5-chloro-2-pentyloxynicotinamido>-ethyl)-benzenesulfonamide (m.p. 170°–171° C.);

N-[4-(2-<5-chloro-2-pentyloxy-nicotinamido>-ethyl)-benzenesulfonyl]-N'-methyl urea of m.p. 181°–183° C. (from ethanol);

N-[4-(2-<5-chloro-2-pentyloxy-nicotinamido>-ethyl)-benzenesulfonyl]-N'-propyl urea of m.p. 150°–151° C. (from methanoldioxane);

N-[4-(2-<5-chloro-2-pentyloxy-nicotinamido>-ethyl)-benzenesulfonyl]-N'-ethyl urea of m.p. 112°–114° C. (from ethanol);

N-[4-(2-<5-chloro-2-pentyloxy-nicotinamido>-ethyl)-benzenesulfonyl]-N'-(4-methylcyclohexyl) urea of m.p. 155°–156° C. (from methanol-dioxane);

N-[4-(2-<5-chloro-2-pentyloxy-nicotinamido>-ethyl)-benzenesulfonyl]-N'-butyl urea of m.p. 141°–143° C. (from ethanol);

N-[4-(2-<5-chloro-2-pentyloxy-nicotinamido>-ethyl)-benzenesulfonyl]-N'-(4-ethylcyclohexyl) urea of m.p. 134°–136° C. (from ethanol).

In analogous manner there are obtained from 4-(2-<2-propoxy-nicotinamido>-ethyl)-benzenesulfonamide (m.p. 168°–169° C.)

N-[4-(2-<2-propoxy-nicotinamido>-ethyl)-benzenesulfonyl]-N'-cyclohexyl urea of m.p. 151°–152° C. (from methanol);

N-[4-(2-<2-propoxy-nicotinamido>-ethyl)-benzenesulfonyl]-N'-methyl urea of m.p. 200°–201° C. (from methanol-dimethylformamide).

In analogous manner there are obtained from 4-(2-<5-chloro-2-propoxy-nicotinamido>-ethyl)-benzenesulfonamide (m.p. 206°–207° C.)

N-[4-(2-<5-chloro-2-propoxy-nicotinamido>-ethyl)-benzenesulfonyl]-N'-cyclohexyl urea of m.p. 156°–157° C. (from methanol);

N-[4-(2-<5-chloro-2-propoxy-nicotinamido>-ethyl)-benzenesulfonyl]-N'-methyl urea of m.p. 190°–191° C. (from methanol-dimethylformamide).

In analogous manner there are obtained from 4-(2-<2-butoxy-nicotinamido>-ethyl)-benzenesulfonamide of m.p. 151°-152° C.

N-[4-(2-<2-butoxy-nicotinamido>-ethyl)-benzenesulfonyl]-N'-methyl urea of m.p. 191°-192° C. (from methanol).

In analogous manner there are obtained from
4-(2-<5-chloro-2-octyloxy-nicotinamido>-ethyl)-benzenesulfonamide of m.p. 124°-125° C.

N-[4-(2-<5-chloro-2-octyloxy-nicotinamido>-ethyl)-benzenesulfonyl]-N'-methyl urea of m.p. 151°-152° C. (from ethanol);

N-[4-<2-(2-butoxy-5-chloro-nicotinamido>-ethyl)-benzenesulfonyl]-N'-cyclooctyl urea of m.p. 130°-132° C. (from dilute methanol);

N-[4-<2-(2-butoxy-5-chloro-nicotinamido>-ethyl)-benzenesulfonyl]-N'-(bicyclo[2,2,1]hept-2-yl) urea of m.p. 177°-179° C. (from dilute isopropanol);

N-[4-<2-(5-chloro-2-pentyloxy-nicotinamido)-ethyl>-benzenesulfonyl]-N'-cyclohexyl urea of m.p. 152°-153° C. (from ethanol);

from 2-(4-chloro-phenoxy)-nicotinic acid of m.p. 159°-160° C. by passing over 4-(2-<2-(4-chloro-phenoxy)-nicotinamido>-ethyl)-benzenesulfonamide of m.p. 192°-194° C.;

N-[4-<2-(2-<4-chloro-phenoxy>-nicotinamido)-ethyl>-benzenesulfonyl]-N'-cyclohexyl urea of m.p. 175°-177° C. (from dilute ethanol);

N-(4-<2-(2-<4-chloro-phenoxy>-nicotinamido)-ethyl>-benzenesulfonyl)-N'-butyl urea of m.p. 120°-122° C. (from dilute ethanol);

N-(4-<2-(2-<4-chloro-phenoxy>-nicotinamido)-ethyl>-benzenesulfonyl)-N'-(4-methyl-cyclohexyl) urea of m.p. 175°-177° C. (from isopropanol);

from 2-(4-methyl-phenoxy)-nicotinic acid of m.p. 146°-148° C. by passing over 4-(2-<2-(4-methyl-phenoxy)-nicotinamido>-ethyl)-benzenesulfonamide of m.p. 163°-165° C., N-(4-<2-(2-<4-methyl-phenoxy>-nicotinamido)-ethyl>-benzenesulfonyl)-N'-cyclohexyl urea of m.p. 167°-169° C. (from dilute ethanol);

N-(4-<2-(2-<4-methyl-phenoxy>-nicotinamido)-ethyl>-benzenesulfonyl)-N'-(4-methyl-cyclohexyl) urea of m.p. 162°-164° C. (from dilute ethanol);

N-(4-<2-(2-<4-methyl-phenoxy>-nicotinamido)-ethyl>-benzenesulfonyl)-N'-butyl urea of m.p. 152°-154° C. (from methanol);

from 2-(4-methoxy-phenoxy)-nicotinic acid of m.p. 179°-180° C. by passing over 4-(2-<2-(4-methoxy-phenoxy)-nicotinamido>-ethyl)-benzenesulfonamide of m.p. 135°-137° C.

N-(4-<2-(2-<4-methyl-phenoxy>-nicotinamido)-ethyl>-benzenesulfonyl)-N'-cyclohexyl urea of m.p. 167°-169° C. (from dilute ethanol);

N-(4-<2-(2-<4-methyl-phenoxy>-nicotinamido)-ethyl>-benzenesulfonyl)-N'-butyl urea of m.p. 130°-132° C. (from dilute ethanol);

N-(4-<2-(2-<4-methoxy-phenoxy>-nicotinamido)-ethyl>-benzenesulfonyl)-N'-(4-methyl-cyclohexyl) urea of m.p. 162°-164° C. (from methanol);

from 2-phenoxy-nicotinic acid of m.p. 182°-184° C., by passing over 4-(2-<2-phenoxy-nicotinamido>-ethyl)-benzenesulfonamide of m.p. 159°-161° C., N-(4-<2-(2-phenoxy-nicotinamido)-ethyl>-benzenesulfonyl)-N'-benzyl urea of m.p. 177°-179° C. (from dilute ethanol);

N-(4-<2-(2-phenoxy-nicotinamido)-ethyl>-benzenesulfonyl)-N'-(4-methyl-cyclohexyl) urea of m.p. 158° C. (from dilute ethanol);

N-(4-<2-(2-phenoxy-nicotinamido)-ethyl>-benzenesulfonyl)-N'-butyl urea of m.p. 155°-156° C. (from dilute ethanol);

from 5-chloro-2-isobutoxy-nicotinic acid of m.p. 121°-123° C. by passing over 4-(2-<5-chloro-2-isobutoxy-nicotinamido>-ethyl)-benzenesulfonamide of m.p. 193°-195° C., N-(4-<2-(5-chloro-2-isobutoxy-nicotinamido)-ethyl>-benzene sulfonyl)-N'-cyclohexyl urea of m.p. 174°-176° C. (from methanol);

N-(4-<2-(5-chloro-2-isobutoxy-nicotinamido)-ethyl>-benzene sulfonyl)-N'-butyl urea of m.p. 172°-174° C. (from methanol);

N-(4-<2-(5-chloro-2-isobutoxy-nicotinamido)-ethyl>-benzene sulfonyl)-N'-ethyl urea of m.p. 172°-174° C. (from methanol);

from 5-chloro-2-cyclopentyloxy-nicotinic acid of m.p. 102°-104° C. by passing over 4-(2-<5-chloro-2-cyclopentyloxy-nicotinamido>-ethyl)-benzenesulfonamide of m.p. 219°-221° C., N-(4-<2-(5-chloro-2-cyclopentyloxy-nicotinamido)-ethyl>-benzenesulfonyl)-N'-cyclohexyl urea of m.p. 179°-181° C. (from dilute ethanol);

N-(4-<2-(5-chloro-2-cyclopentyloxy-nicotinamido)-ethyl>-benzenesulfonyl)-N'-(4-methyl-cyclopentyl) urea of m.p. 173°-175° C. (from dilute ethanol);

N-(4-<2-(5-chloro-2-cyclopentyloxy-nicotinamido)-ethyl>-benzenesulfonyl)-N'-butyl urea of m.p. 168°-170° C. (from dilute ethanol);

from 5-chloro-2-cyclohexylmethoxy-nicotinic acid of m.p. 150°-151° C., by passing over 4-(2-<5-chloro-2-cyclohexylmethoxy-nicotinamido>-ethyl)-benzenesulfonamide of m.p. 170°-172° C.;

N-(4-<2-(5-chloro-2-cyclohexylmethoxy-nicotinamido)-ethyl>-benzenesulfonyl)-N'-butyl urea of m.p. 168°-170° C. (from methanol);

from 5-chloro-2-(4-methyl-cyclohexyloxy)-nicotinic acid of m.p. 93°-95° C., by passing over 4-(2-<5-chloro-2-(4-methyl-cyclohexyloxy)nicotinamido>-ethyl)-benzenesulfonamide of m.p. 223°-225° C.;

N-(4-<2-(5-chloro-2-<4-methyl-cyclohexyloxy>-nicotinamido)ethyl>-benzenesulfonyl)-N'-cyclohexyl urea of m.p. 125°-127° C. (from methanol);

N-(4-<2-(5-chloro-2-<4-methyl-cyclohexyloxy>-nicotinamido)ethyl>-benzenesulfonyl)-N'-butyl urea of m.p. 164°-165° C. from methanol);

N-(4-<2-(5-chloro-2-cyclohexylmethoxy-nicotinamido)-ethyl>-benzenesulfonyl)-N'-ethyl urea of m.p. 167°-169° C. (from dilute methanol);

from 2-butoxy-6-methyl-nicotinic acid of m.p. 52°-54° C. prepared from 2-chloro-6-methyl-nicotinic acid and sodium butylate, by passing over 4-(2-<2-butoxy-6-methyl-nicotinamido>-ethyl)-benzenesulfonamide of m.p. 165°-166° C., N-(4-<2-(2-butoxy-6-methyl-nicotinamido)-ethyl>-benzenesulfonyl)-N'-butyl urea of m.p. 118°-121° C. (from dilute methanol);

from 2-butoxy-6-methyl-nicotinic acid by chlorination 2-butoxy-5-chloro-6-methyl-nicotinic acid of m.p. 95° to 97° C. and from the latter by passing over 4-(2-<2- butoxy-5-chloro-6-methyl-nicotinamido>-ethyl)-benzenesulfonamide of m.p. 183°–184° C., N-(4-<2-(2-butoxy-5-chloro-6-methyl-nicotinamido)-ethyl>-benzenesulfonyl)-N'-cyclohexyl urea of m.p. 136°–138° C. (from dilute methanol);

N-(4-<2-(2-butoxy-5-chloro-6-methyl-nicotinamido)-ethyl>-benzenesulfonyl)-N'-butyl urea of m.p. 153°–155° C. (from acetic acid ester);

N-(4-<2-(2-butoxy-5-chloro-6-methyl-nicotinamido)-ethyl>-benzenesulfonyl)-N'-ethyl urea of m.p. 155°–157° C. (from dilute methanol);

from 2-cyclohexyloxy-6-methyl-nicotinic acid (m.p. 96°–98° C., prepared from 2-chloro-6-methyl-nicotinic acid and cyclohexanol sodium), by passing over 4-(2-<2-cyclohexyloxy-6-methyl-nicotinamido>-ethyl)-benzene-sulfonamide of m.p. 170°–172° C., N-(4-<2-(2-cyclohexyloxy-6-methyl-nicotinamido)-ethyl>-benzenesulfonyl)-N'-ethyl urea of m.p. 156°–158° C. (from dilute methanol);

N-(4-<2-(2-cyclohexyloxy-6-methyl-nicotinamido)-ethyl>-benzenesulfonyl)-N'-butyl urea of m.p. 140°–143° C. (from dilute methanol);

from 2-cyclohexyloxy-nicotinic acid (m.p. 57°–58° C., by chlorination 5-chloro-2-cyclohexyloxy-nicotinic acid of m.p. 65°–67° C. and from the latter, by passing over 4-(2-<-5-chloro-2-cyclohexyloxy-nicotinamido>-ethyl)-benzenesulfonamide of m.p. 159°–161° C., N-(4-<2-(5-chloro-2-cyclohexyloxy-nicotinamido>-ethyl)-benzenesulfonyl)-N'-cyclohexyl urea of m.p. 190°–191° C. (from ethanol);

N-(4-<2-(5-chloro-2-cyclohexyloxy-nicotinamido>-ethyl)-benzenesulfonyl)-N'-methyl urea of m.p. 186°–188° C. (from methanol-dioxane);

from 2-benzyloxy-nicotinic acid of m.p. 104°–106° C., by passing over 4-(2-<2-benzyloxy-nicotinamido>-ethyl)-benzene-sulfonamide of m.p. 167°–168° C., N-(4-<2-(2-benzyloxy-nicotinamido>-ethyl)-benzenesulfonyl)-N'-cyclohexyl urea of m.p. 160°–162° C. (from ethanol);

N-(4-<2-(2-benzyloxy-nicotinamido>-ethyl)-benzenesulfonyl)-N'-methyl urea of m.p. 192°–194° C. (from ethanol);

N-(4-<2-(2-benzyloxy-nicotinamido>-ethyl)-benzenesulfonyl)-N'-(4-methyl-cyclohexyl) urea of m.p. 154°–156° C. (from ethanol);

N-(4-<2-(2-benzyloxy-nicotinamido>-ethyl)-benzenesulfonyl)-N'-butyl urea of m.p. 145°–147° C. (from ethanol);

from 2-isobutyloxy-6-methyl-nicotinic acid (m.p. 84°–86° C., prepared from 2-chloro-6-methyl-nicotinic acid and sodium isobutylate), by passing over 4-(2<2-isobutyloxy-6-methyl-nicotinamido>-ethyl)-benzenesulfonamide of m.p. 174°–176° C., N-(4-<2-(2-isobutyloxy-6-methyl-nicotinamido)-ethyl>-benzenesulfonyl)-N'-ethyl urea of m.p. 172°–174° C. (from dilute methanol);

N-(4-<2-(2-isobutyloxy-6-methyl-nicotinamido)-ethyl>-benzenesulfonyl)-N'-butyl urea of m.p. 120°–123° C. (from dilute methanol);

N-(4-<2-(2-isobutyloxy-6-methyl-nicotinamido)-ethyl>-benzenesulfonyl)-N'-cyclohexyl urea of m.p. 167°–169° C. (from dilute methanol);

from 5-chloro-2-isobutyloxy-6-methylnicotinic acid (m.p. 114°–116° C., prepared from 2-isobutyloxy-6-methyl-nicotinic acid by chlorination), by passing over 4-(2-<5-chloro-2-isobutyloxy-6-methyl-nicotinamido>-ethyl)-benzenesulfonamide of m.p. 191°–193° C., N-(4-<2-(5-chloro-2-isobutyloxy-6-methyl-nicotinamido)-ethyl>-benzenesulfonyl)-N'-ethyl urea of m.p. 169°–172° C. (from dilute methanol);

N-(4-<2-(5-chloro-2-isobutyloxy-6-methyl-nicotinamido)-ethyl>-benzenesulfonyl)-N'-butyl urea of m.p. 170°–173° C. (from dilute methanol);

from 5-chloro-2-cyclohexylmethoxy-6-methyl-nicotinic acid (m.p. 137°–140° C., prepared from 2-cyclohexylmethoxy-6-methylnicotinic acid of m.p. 100°–103° C. by chlorination), by passing over 4-(2-<5-chloro-2-cyclohexylmethoxy-6-methyl-nicotinamido>-ethyl)-benzenesulfonamide of m.p. 197°–199° C., N-(4-<2-(5-chloro-2-cyclohexylmethoxy-6-methyl-nicotinamido)-ethyl>-benzenesulfonyl)-N'-ethyl urea of m.p. 167°–169° C. (from dilute methanol);

N-(4-<2-(5-chloro-2-cyclohexylmethoxy-6-methyl-nicotinamido)-ethyl>-benzenesulfonyl)-N'-butyl urea of m.p. 137°–139° C. (from dilute methanol);

from 6-methyl-2-phenoxy-nicotinic acid (m.p. 154°–156° C., prepared from 2-chloro-6-methyl-nicotinic acid and Na-phenolate), by passing over 4-(2-<6-methyl-2-phenoxy-nicotinamdio>-ethyl)-benzene-sulfonamide of m.p. 180°–182° C., N-(4-<2-(6-methyl-2-phenoxy-nicotinamido>-ethyl-benzenesulfonyl)-N'-ethyl urea of m.p. 149°–152° C. (from dilute methanol);

N-(4-<2-(6-methyl-2-phenoxy-nicotinamido>-ethyl-benzenesulfonyl)-N'-butyl urea of m.p. 155°–157° C. (from dilute methanol).

EXAMPLE 2

N-[4-(2-<2-butoxy-nicotinamido>ethyl)-benzenesulfonyl]-N'-cyclohexyl urea 3.9 g of 2-butoxy-nicotinic acid are dissolved together with 8.4 ml of triethylamine in 150 ml of tetrahydrofuran. After cooling to 0° C., 2.0 ml of chloroformic acid methyl ester are slowly added dropwise while stirring. The mixture is stirred for 30 minutes at 0° C., thereafter 6.3 g of N-[4-(2-aminoethyl)-benzenesulfonyl]-N'-cyclohexyl urea are added portionswise and the mixture is stirred for 1 hour at 0° C. and for 4 hours at room temperature. The suspension is concentrated in vacuo, the residue is taken up in water and the solution is filtered and acidified with dilute acetic acid. The precipitate formed in this process is suction-filtered, and reprecipitated from dilute ammonia solution with dilute acetic acid. The N-[4-(2-<2-butoxy-nicotinamido>-ethyl)-benzenesulfonyl]-N'-cyclohexyl urea melts at a temperature of from 141° to 142° C. after having been recrystallized from methanol.

In analogous is obtained from 2-phenoxy-nicotinic acid N-[4-(2-<2-phenoxy-nicotinamido>-ethyl)-benzenesulfonyl]-N'-cyclohexyl urea of m.p. 124°–125° C. (from acetic acid) ethyl ester-methanol).

In analogous manner is obtained from 2-pentyloxy-nicotinic acid

N-(4-<2-(2-pentyloxy-nicotinamido)-ethyl>-benzenesulfonyl) N'-cyclohexyl urea of m.p. 154°–155° C. (from dilute ethanol); from 2-cyclohexyloxy-nicotinic acid (m.p. 57°–58° C., prepared from 2-chloro-nicotinic acid and cyclohexanol-sodium) N-(4-<2-(2-cyclohexyloxy-nicotinamido)-ethyl>-benzenesulfonyl)-N'-cyclohexyl urea of m.p. 116°–120° C. (reprecipitated from acetic acid ester-diisopropyl ether)

EXAMPLE 3

N-[4-(2-<2-butoxy-5-chloro-nicotinamido>ethyl)-benzenesulfonyl]-N'-hexyl urea 4.7 g of 4-(2-<2-butoxy-5-chloro-nicotinamido>-ethyl)benzenesulfonyl-carbamic acid methyl ester (m.p. 164°–166° C., prepared from 4-(2-<2-butoxy-5-chloro-nicotinamido>-ethyl)-benzenesulfonamide and chloroformic acid methyl ester) are heated to the boil for 2 hours with 1.0 g of n-hexylamine in 50 ml of dioxane at the descending condenser. Thereafter the solvent is evaporated off in vacuo, the residue is reprecipitated from dilute ammonia solution with dilute acetic acid and recrystallized from chloroform/methanol.

The N-[4-(2-<2-butoxy-5-chloro-nicotinamido>-ethyl)-benzenesulfonyl]-N'-hexyl urea thus prepared melts at 134°–136° C.

In analogous manner is obtained

N-(4-<2-(2-butoxy-5-chloro-nicotinamido)-ethyl>-benzenesulfonyl)-N'-3-methyl-cyclopentyl urea of m.p. 110°–111° C. (from dilute ethanol);

from 4-<2-(2-phenoxy-nicotinamido)-ethyl>-benzenesulfonylcarbamic acid methyl ester (m.p. 176°–178° C., prepared from 4-<2-(2-phenoxy-nicotinamido)-ethyl>-benzenesulfonamide and chloroformic acid methyl ester);

N-(4-<2-(2-phenoxy-nicotinamido)-ethyl>-benzenesulfonyl)-N'-cyclopentyl urea of m.p. 179°–181° C. (from dilute ethanol);

N-(4-<2-(2-phenoxy-nicotinamido)-ethyl>-benzenesulfonyl)-N'-(3-methyl-cyclopentyl) urea of m.p. 158°–160° C. (in dilute ethanol);

N-(4-<2-(2-phenoxy-nicotinamido)-ethyl>-benzenesulfonyl)-N'-cyclopentylmethyl urea of m.p. 142°–144° C. (in dilute methanol).

What is claimed is:

1. Benzenesulfonylurea of the formula

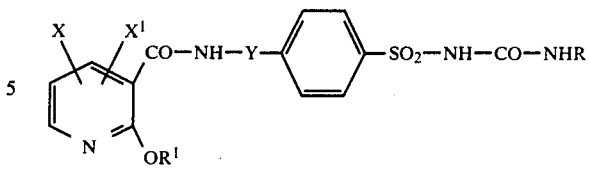

in which
R$_1$ is alkyl with 3 to 8 carbon atoms, cycloalkyl, cycloalkylalkyl, alkylcycloalkyl, each of which having of from 5 to 9 carbon atoms, phenyl, which may be mono- or disubstituted by alkyl or alkoxy each of which having up to 4 carbon atoms, or by halogen, phenylalkyl with up to 3 carbon atoms in the alkyl moiety, which may be mono- or di-substituted in the phenyl nucleus by alkyl or alkoxy each having up to 4 carbon atoms, or by halogen,
X and X$^1$ each is hydrogen, alkyl with up to 4 carbon atoms, alkoxy with up to 2 carbon atoms, halogen,
Y is alkylene with 2 to 3 carbon atoms,
R is alkyl with 1 to 6 carbon atoms, cycloalkyl, alkylcycloalkyl, cycloalkylalkyl, cycloalkenyl, alkylcycloalkenyl each having of from 5 to 9 carbon atoms, alkylcyclopentylmethyl, cyclohexenylmethyl, chlorocyclohexyl, bicycloheptenylmethyl, bicycloheptylmethyl, bicycloheptenyl, bicycloheptyl, nortricyclyl, adamantyl, benzyl
or a physiologically acceptable salt thereof.

2. A compound as claimed in claim 1 wherein Y is the group —CH$_2$CH$_2$—.

3. Method of using a benzenesulfonylurea as claimed in claim 1 or one of its salts for the treatment of diabetes.

4. The compound of claim 1 which is N-(4-<2-(2-butoxy-5-chloro-6-methyl-nicotinamido)-ethyl>-benzenesulfonyl)-N'-butyl urea.

5. The compound of claim 1, which is N-[4-(2-<2-phenoxy-nicotinamido>-ethyl)-benzenesulfonyl]-N'-cyclohexylurea.

6. The compound of claim 1, which is N-[4-(2-<5-chloro-2-pentyloxy-nicotinamido>-ethyl)-benzenesulfonyl]-N'-propyl urea.

7. The compound of claim 1, which is N-(4-<2-(5-chloro-2-isobutyloxy-6-methyl-nicotinamido)-ethyl>-benzenesulfonyl)-N'-butylurea.

8. Pharmaceutical preparation for the treatment of diabetes mellitus containing a hypoglycemically effective amount of a benzenesulfonylurea as defined in claim 1 or a salt thereof.

9. A process for the treatment of diatetes mellitus which comprises administering orally to a patient a hypoglycemically efffective amount of a benzenesulfonylurea as defined in claim 1 or a salt thereof.

* * * * *